United States Patent [19]

McCurdy

[11] Patent Number: 4,531,317
[45] Date of Patent: Jul. 30, 1985

[54] PORTABLE VIEWING APPARATUS

[75] Inventor: Frederic McCurdy, Newburgh, N.Y.

[73] Assignee: Graphic Technology, Inc., Newburgh, N.Y.

[21] Appl. No.: 618,534

[22] Filed: Jun. 8, 1984

[51] Int. Cl.³ .............................................. G09F 9/00
[52] U.S. Cl. .................................... 40/366; 40/152.2; 40/574
[58] Field of Search .................... 40/152.1, 152.2, 361, 40/564, 341, 124.1, 365, 366

[56] References Cited

U.S. PATENT DOCUMENTS

| | | | |
|---|---|---|---|
| 445,174 | 1/1891 | Hagelberg | 40/152.2 |
| 2,637,131 | 5/1953 | Paulson | 40/152.2 |
| 2,646,636 | 7/1953 | Gandee | 40/152.2 |
| 2,795,967 | 6/1957 | Walker | 40/365 |
| 3,499,240 | 3/1970 | Cotton et al. | 40/443 |
| 3,748,455 | 7/1973 | Welton | 240/2 AT |
| 3,888,564 | 6/1975 | Lebow | 60/366 |
| 3,964,193 | 6/1976 | Gerhardt | 40/361 X |
| 3,982,344 | 9/1976 | Phillips | 40/564 |
| 4,136,380 | 1/1979 | Shaw | 33/109 |
| 4,152,852 | 5/1979 | Brown | 40/361 |
| 4,164,822 | 8/1979 | Batton | 40/361 |
| 4,373,280 | 2/1983 | Armfield | 40/361 |

OTHER PUBLICATIONS

ANSI PH 2/31/1969 American National Standard Direct Viewing of Photographic Transparencies (Color).
ANSI PH 2/32/1972 American National Viewing Conditions for the Appraisal of Color Quality and Color Uniformity in the Graphic Arts.
A Portable Viewing Booth–Ingara Enterprics Inc., 10-5-1983.
An Undated Publication entitled Graphic Light Color Viewing.

Primary Examiner—Gene Mancene
Assistant Examiner—Wenceslao J. Contreras
Attorney, Agent, or Firm—Felfe & Lynch

[57] ABSTRACT

A portable apparatus for simultaneously viewing a transparency and a reflection copy image. The apparatus preferably complies with American National Standard Institute standards "Direct Viewing of Photographic Color Transparencies" and "Viewing Conditions for the Appraisal of Color Quality and Color Uniformity in the Graphic Arts." The apparatus includes a case which opens to have a cover portion positioned approximately horizontally near the top of an approximately vertical body portion. Pivotal side light shield plates can be opened to shield the sides of the apparatus from undesired ambient light, and a pivotal bottom plate can be positioned approximately horizontally for viewing prints. A transparency viewing plate having back lighting means for illuminating a transparency is positioned within-the field of light from a source in the cover portion which strikes both the transparency and simultaneously the reflection copy image on the approximately horizontal plate.

8 Claims, 5 Drawing Figures

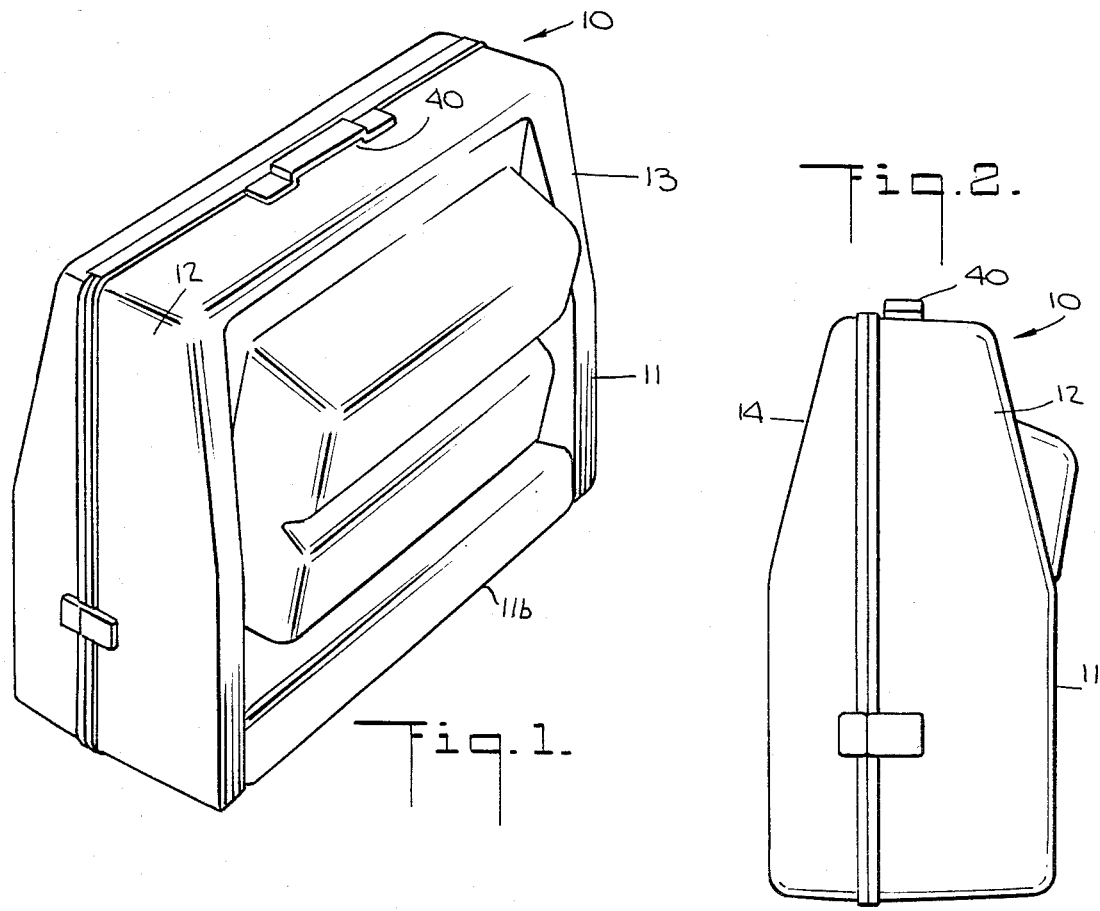
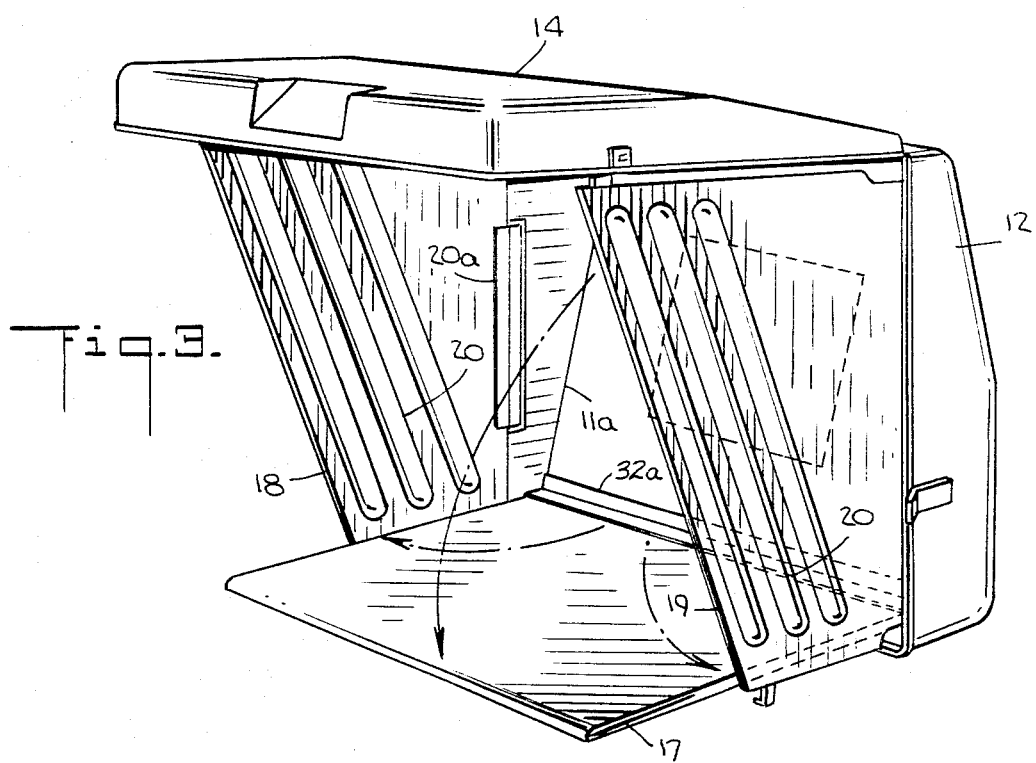

PORTABLE VIEWING APPARATUS

This invention relates to portable apparatus for simultaneously viewing a transparency and a reflection copy image. As used herein, the term "transparency" includes transparent or translucent positives or images through which light must pass. The term reflection copy image includes a front-viewed picture or other reflection subject matter such as, for example, a proof or print.

One prior apparatus for simultaneously viewing transparencies and reflection copy pictures is a stationary viewing station which accomodates a standard transparency viewer and into which a transparency viewer may be recessed. This viewing station has the limitation that it is not portable.

One prior portable apparatus for simultaneously viewing transparencies and reflection copy images has the disadvantage that in one embodiment the portions of the apparatus must be inclined toward one another which makes viewing awkward. In another embodiment a light source requires adjustment to a position for illuminating both the reflection copy image and the transparency.

Another portable viewing apparatus for viewing only reflection copy images has the disadvantage that transparencies and reflection copy images cannot be simultaneously viewed and compared for color quality and uniformity.

It is an object of the present invention, therefore, to provide a new and improved portable apparatus for simultaneously viewing a transparency and a reflection copy image which avoids one or more of the disadvantages and limitations of prior viewing apparatus.

It is another object of the invention to provide a new and improved portable apparatus for simultaneously viewing a transparency and a reflection copy image which is housed in a protective case.

It is another object of the invention to provide a new and improved portable apparatus for simultaneously viewing a transparency and a reflection copy image in which the transparency is viewable at a convenient oblique angle with respect to the reflection copy image.

It is another object of the invention to provide a new and improved apparatus for simultaneously viewing a transparency and a reflection copy image which comply with American National Standard Institute standards, namely, ANSI PH2.31-1969 (R 1982) "Direct Viewing of Photographic Color Transparencies" and ANSI PH2.32-1972 (R 1981) "Viewing Conditions for the Appraisal of Color Quality and Color Uniformity in the Graphic Arts."

In accordance with the invention, a portable apparatus for simultaneously viewing a transparency and a reflection copy image comprises a portable case having a body portion having sides and adapted to stand approximately vertically and having a cover portion pivotally coupled to the body portion near the top of the body portion for approximately horizontal disposition upon opening the case. The apparatus includes a pair of side light-shield means individually pivotally coupled to the sides of the body portion for moving outwardly from the body portion to an approximately vertical disposition extending from the sides of the body portion. The apparatus also includes means pivotally coupled to the body portion approximately at the bottom thereof for moving outwardly from the body portion for approximately horizontal disposition. The body portion has a transparency viewing portion including back-lighting means for illuminating a transparency when disposed therein from behind. The cover portion includes lighting means for illuminating a reflection copy image when disposed on the approximately horizontally disposed means and for simultaneously illuminating the front of the transparency in the body portion.

For a better understanding of the present invention, together with other and further objects thereof, reference is made to the following description, taken in connection with the accompanying drawings, and its scope will be pointed out in the appended claims.

Referring now to the drawings:

FIG. 1 is a perspective view of portable apparatus for simultaneously viewing a transparency and a reflection copy image, constructed in accordance with the invention;

FIG. 2 is a side elevational view of the FIG. 1 apparatus;

FIG. 3 is a perspective view of the FIG. 1 apparatus in a fully open position;

FIG. 4 is a front elevational view of the FIG. 1 apparatus in an operable open position; and FIG. 5 is a sectional view of the FIG. 1 apparatus, taken along line 5—5 of FIG. 4.

Referring now more particularly to FIGS. 1 and 2 of the drawings, a portable apparatus for simultaneously viewing a transparency and a reflection copy image, constructed in accordance with the invention, comprises a portable case 10 having a body portion 11, preferably of a suitable plastic material, having sides 12, 13 and adapted to stand approximately vertically. The portable case 10 has a cover portion 14, also preferably of the same plastic material, pivotally coupled to the body portion near the top of the body portion for approximately horizontal disposition upon opening the case as represented in FIGS. 3, 4 and 5.

The cover portion 14 and the body portion 11 include hinged interconnections 16 (FIG. 5) for moving the cover portion to the approximately horizontal disposition.

The apparatus also includes a pair of side light-shield means 18, 19 individually pivotally coupled to the sides 12, 13 of the body portion 11 for moving outwardly from the body portion 11 to an approximately vertical disposition extending from the sides of the internal member 11a of the body portion 11. The pair of light-shield means 18, 19 preferably comprise opaque plates having reinforcing ribs 20 and connected by any suitable hinges, for example, hinge 20a, to the sides of the internal member 11a. As represented in FIG. 4, the plates 18, 19 are effective to support the cover portion 14 in its approximately horizontal disposition by means of connectors 32, 33 in the cover portion 14 which rest on the tops of the plates 18, 19.

The apparatus also includes means 17 pivotally coupled to an internal member 11a, which is attached to and included in the body portion 11, approximately at the bottom of body portion 11, for moving outwardly from the body portion 11 for approximately horizontal disposition onto a pivotal member 32a, as represented in FIG. 3. The first means 17 preferably comprises a plate on which a reflection image may be placed between the side plates 18, 19. The term "approximately horizontal" disposition when referring to the plate 17 includes small angular dispositions of less than 25 degrees, for exam-

United States Patent [19]

Chang et al.

[11] Patent Number: 4,531,318
[45] Date of Patent: Jul. 30, 1985

[54] DISPLAY OR INDICATING ELEMENT WITH BENT CORE

[75] Inventors: Kwangling Chang, Toronto; Dalpat D. Mistry, Mississauga, both of Canada

[73] Assignee: NEI Canada Limited, Ontario, Canada

[21] Appl. No.: 532,771

[22] Filed: Sep. 16, 1983

[51] Int. Cl.³ .............................................. G09F 9/00
[52] U.S. Cl. ...................................... 40/449; 40/447; 340/815.05; 340/815.27
[58] Field of Search ............... 340/815.26, 815.27, 340/815.04, 815.05; 40/449, 447, 450

[56] References Cited

U.S. PATENT DOCUMENTS

| | | | |
|---|---|---|---|
| 3,295,238 | 1/1967 | Winrow | 40/449 |
| 3,365,824 | 1/1968 | Winrow | 40/449 |
| 3,518,664 | 6/1970 | Taylor | 340/815.26 |
| 3,942,274 | 3/1976 | Winrow | 40/449 |
| 4,178,575 | 12/1979 | Ono | 340/815.04 |
| 4,243,978 | 1/1981 | Winrow | 340/815.26 |

Primary Examiner—Gene Mancene
Assistant Examiner—Cary E. Stone

[57] ABSTRACT

A thin disk contrastingly colored on opposite sides is rotatably mounted to rotate about its diameter. A permanent magnet on the disk allows the disk to be driven by a pair of reversibly magnetizable cores. One of the cores is bent to provide a stop which limits the rotation of the disk in either direction. The two limiting positions correspond to the display of the contrastingly colored sides in the viewing direction.

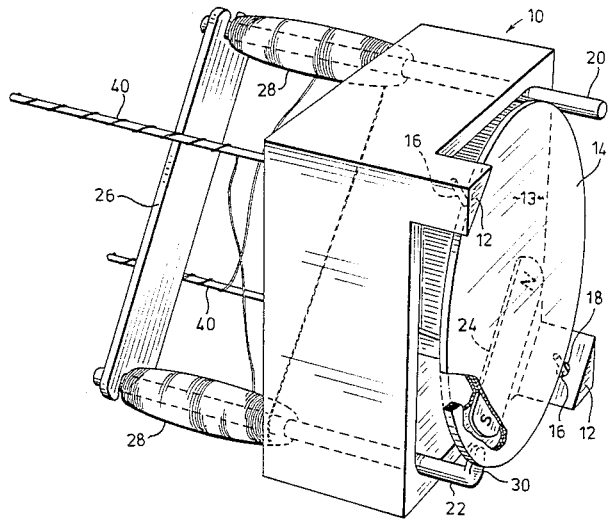

16 Claims, 3 Drawing Figures